(12) United States Patent
Althaus et al.

(10) Patent No.: US 11,674,617 B2
(45) Date of Patent: Jun. 13, 2023

(54) TUBE LOCK

(71) Applicant: Horizon Healthcare LLC, Dayton, OH (US)

(72) Inventors: Joseph H. Althaus, Yellow Springs, OH (US); Ryan Muhlenkamp, Bellbrook, OH (US); Matthew B. Sunday, California, KY (US)

(73) Assignee: Horizon Healthcare LLC, Dayton, OH (US)

( * ) Notice: Subject to any disclaimer, the term of this patent is extended or adjusted under 35 U.S.C. 154(b) by 281 days.

(21) Appl. No.: 17/090,996

(22) Filed: Nov. 6, 2020

(65) Prior Publication Data

US 2021/0199215 A1 Jul. 1, 2021

Related U.S. Application Data

(60) Provisional application No. 62/954,175, filed on Dec. 27, 2019.

(51) Int. Cl.
| | |
|---|---|
| *F16K 7/04* | (2006.01) |
| *F16L 3/10* | (2006.01) |
| *A61M 25/02* | (2006.01) |

(52) U.S. Cl.
CPC ............ *F16L 3/1075* (2013.01); *A61M 25/02* (2013.01); *F16K 7/04* (2013.01); *A61M 2025/024* (2013.01)

(58) Field of Classification Search
CPC ...... F16L 3/2235; F16K 7/04; B60R 16/0215; A61M 25/02; A61M 2025/024
See application file for complete search history.

(56) References Cited

U.S. PATENT DOCUMENTS

| | | | | |
|---|---|---|---|---|
| 2,650,948 A | * | 9/1953 | Findlay | F16L 3/2235 |
| | | | | 248/68.1 |
| 4,840,333 A | * | 6/1989 | Nakayama | F16B 5/12 |
| | | | | 248/68.1 |

(Continued)

FOREIGN PATENT DOCUMENTS

| | | |
|---|---|---|
| EP | 2464406 B1 | 10/2016 |
| WO | 2014/144557 A2 | 9/2014 |

(Continued)

OTHER PUBLICATIONS

U.S. Appl. No. 17/090,987, filed Nov. 6, 2020, entitled "Tube Clamp", Joseph H. Althaus et al.

*Primary Examiner* — Umashankar Venkatesan
(74) *Attorney, Agent, or Firm* — Thomas E. Lees, LLC

(57) ABSTRACT

A tube lock includes a lock housing, a clamp cover, and a tube clamp. The lock housing has a tube compartment having an opening therein. In this regard, the clamp cover mates with the lock housing to provide a barrier over the opening of the tube compartment. The tube clamp has a tube entry along a major surface thereof. A first tube passageway extends from the tube entry into the housing, and a tube receiving channel is coupled to the first tube passageway. The tube clamp also comprises a clamping mechanism having a lever handle, and a tube pinch that is coupled to the lever handle. When the clamp cover is mated with the lock housing, the lever handle of the clamping mechanism is prevented from transitioning from the second position to the first position, thus locking the tube inserted into the tube clamp.

19 Claims, 17 Drawing Sheets

(56) References Cited

U.S. PATENT DOCUMENTS

| | | | |
|---|---|---|---|
| 4,899,964 A * | 2/1990 | Sick | F16L 3/2235 248/68.1 |
| 5,029,782 A * | 7/1991 | Andre | F16L 3/2235 248/68.1 |
| 5,535,969 A * | 7/1996 | Duffy, Jr. | F16L 3/237 248/68.1 |
| 6,089,513 A * | 7/2000 | Cau | F16L 3/223 248/68.1 |
| 6,368,315 B1 | 4/2002 | Gillis et al. | |
| 8,361,026 B2 | 1/2013 | Edwards et al. | |
| 8,398,617 B2 | 3/2013 | Ginggen et al. | |
| 8,524,259 B2 | 9/2013 | Taft et al. | |
| 8,882,830 B2 | 11/2014 | Cartledge et al. | |
| 9,079,758 B2 | 7/2015 | O'Dougherty et al. | |
| 9,358,378 B2 | 6/2016 | Hanson et al. | |
| 9,561,354 B2 | 2/2017 | Nebosky et al. | |
| 9,642,996 B2 | 5/2017 | Palmer et al. | |
| 9,743,877 B2 | 8/2017 | Pazart et al. | |
| 10,034,971 B2 * | 7/2018 | Abu-Sultaneh | A61M 1/84 |
| 10,173,018 B1 * | 1/2019 | Rucker | A61M 25/02 |
| 10,295,084 B2 * | 5/2019 | Izawa | F16L 3/237 |
| 10,433,926 B2 * | 10/2019 | Recanati | A61B 50/20 |
| 11,020,566 B2 * | 6/2021 | Beran | A61M 5/1415 |
| 2005/0116122 A1 * | 6/2005 | Nakanishi | F16L 3/223 248/68.1 |
| 2007/0135803 A1 | 6/2007 | Belson | |
| 2009/0043253 A1 | 2/2009 | Podaima | |
| 2009/0118612 A1 | 5/2009 | Grunwald et al. | |
| 2014/0303595 A1 * | 10/2014 | Justus | A61M 5/5086 604/111 |
| 2015/0174320 A1 | 6/2015 | Grant et al. | |
| 2016/0096003 A1 | 4/2016 | Parmar | |
| 2019/0167883 A1 | 6/2019 | Girouard et al. | |
| 2021/0199204 A1 | 7/2021 | Althaus et al. | |

FOREIGN PATENT DOCUMENTS

| | | |
|---|---|---|
| WO | 2014/165727 A1 | 10/2014 |
| WO | 2017/038575 A1 | 3/2017 |
| WO | 2017/087182 A1 | 5/2017 |
| WO | 2018/071651 A1 | 4/2018 |
| WO | 2019/118929 A1 | 6/2019 |

* cited by examiner

TUBE LOCK

CROSS REFERENCE TO RELATED APPLICATIONS

This application claims the benefit of U.S. Provisional Patent Application Ser. No. 62/954,175, filed Dec. 27, 2019, entitled "TUBE LOCK", the disclosure of which is hereby incorporated by reference.

BACKGROUND

Various aspects of the present disclosure relate generally to clamps for flexible tubes, and in particular, to clamp locks for tubes.

Flexible tubes used for channeling fluid flow come in various sizes and are constructed of various materials. For instance, tubes such as catheters used for medical applications, are typically small diameter, hollow, flexible tubes. Catheters are typically constructed of a polymer, such as silicone rubber, nylon, polyurethane, polyethylene terephthalate (PET), latex, etc. Similar tubes also find application in automotive, industrial, robotics, commercial, consumer, and other applications, e.g., to carry fluid in mechanical systems.

BRIEF SUMMARY

According to aspects of the present disclosure, a tube lock comprises a lock housing, a clamp cover, and a tube clamp. The lock housing includes a tube clamp compartment having a clamp compartment opening therein. The clamp cover mates with the lock housing to provide a barrier over the clamp compartment opening of the tube clamp compartment. In some embodiments, the tube clamp can be positioned within, and removed from the tube compartment. In other embodiments, the tube clamp is built in, or is otherwise integral with the lock housing.

Regardless, the tube clamp includes a housing and a clamping mechanism. The housing includes a tube receiving channel therein. In some embodiments, the housing also includes a tube entry along a major surface thereof, and a first tube passageway that extends from the tube entry into the housing and couples to the tube receiving channel. Correspondingly, the clamping mechanism has a lever handle user operable to transition from a first position (e.g., an unlocked/unclamped position) to a second position (e.g., a locked/clamped position), and a tube pinch coupled to the lever handle. Under this configuration, when a tube is positioned in the tube receiving channel, and the lever handle of the clamping mechanism is in the second position, the tube clamp pinches the tube so as to prevent a flow of a fluid through the tube. Moreover, when the clamp cover is mated with the lock housing, the lever handle of the clamping mechanism is prevented from transitioning from the second position to the first position.

According to further aspects of the present disclosure, a tube lock comprises a lock housing and a clamp cover. The lock housing includes a tube clamp compartment, where the tube clamp compartment has a clamp compartment opening therein. The clamp cover mates with the lock housing to provide a barrier over the clamp compartment opening.

In some embodiments, a tube clamp can be positioned within, and removed from the tube compartment. In other embodiments, the tube lock further comprises the tube clamp, which can be built into the lock housing, or is otherwise integral with the lock housing. Regardless, when a tube clamp having a lever handle is in the clamp compartment and the clamp cover is mated with the lock housing, the lever handle is prevented from lifting sufficient to peripherally release a tube held by the tube clamp. In some embodiments, the lever handle is prevented from lifting a sufficient amount to release a clamping/pinching force that prevents fluid flow through a corresponding tube. As such, fluid flow through a pinch point created by the tube clamp is positively prevented when the tube clamp is within the tube clamp compartment and the clamp cover is mated with the lock housing.

In some embodiments, the tube clamp includes a tube receiving channel extending across a tube clamp housing. The tube receiving channel is configured to receive a length of the tube. Moreover, a clamping mechanism has a lever handle that is user operable to transition from a first position, designating an unlocked/unclamped position, to a second position, designating a locked/clamped position. Under this configuration, when a tube is positioned in the tube receiving channel, and the lever handle of the clamping mechanism is in the second position, the tube clamp is in a clamped/locked position, and pinches the tube so as to prevent a flow of a fluid through the tube. Moreover, when the clamp cover is mated with the lock housing, the lever handle of the clamping mechanism is prevented from transitioning from the second position to the first position.

According to yet further aspects of the present disclosure, a tube lock comprises a lock housing, a clamp cover, a linear actuator, a cover lock, electronics, and a tube clamp. The lock housing includes a lock compartment, and a tube clamp compartment having a clamp compartment opening therein. The clamp cover mates with the lock housing to provide a barrier over the clamp compartment opening. The cover lock is positioned in the lock compartment, and the linear actuator controls the ability of the cover lock to transition between a locked state and an unlocked state. More particularly, the cover lock is configured to lock the clamp cover to the lock housing when the cover lock is in the locked state. The electronics within the lock housing are configured to electronically control the linear actuator to transition the cover lock between the locked state and the unlocked state. Here, the electronics include a controller communicably coupled to the linear actuator, and a wireless device communicably coupled to the controller.

In some embodiments, the tube clamp can be positioned within, and removed from the tube compartment. In other embodiments, the tube clamp is built in, or is otherwise integral with the lock housing. Regardless, the tube clamp includes a tube receiving channel extending across a tube clamp housing that is configured to receive a tube. Moreover, the tube clamp includes a clamping mechanism having a lever handle user operable to transition from a first position, designating an unlocked/unclamped position, to a second position, designating a locked/clamped position. Under this configuration, when a tube is positioned in the tube receiving channel and the lever handle of the clamping mechanism is in the second position, the tube clamp pinches the tube so as to prevent a flow of a fluid through the tube. This pinching force also "locks" the tube to the tube clamp so that the tube cannot be extracted from the tube receiving channel. Also, when the clamp cover is mated with the lock housing, the lever handle of the clamping mechanism is prevented from transitioning from the second position to the first position. The lever handle is thus locked in the second position, thus locking the tube inserted into the tube clamp.

Yet further, the controller is configured to control the linear actuator to transition the cover lock from the locked state to the unlocked state, thus unlocking the clamp cover, responsive to an unlock command received from the wireless device, where the unlock command is wirelessly received by the wireless device.

DETAILED DESCRIPTION

Flexible tubes provides a convenient means to contain and enable the flow of fluids in an ordered and directed manner. In this regard, there are applications where is may be desirable to temporarily close off the flow of a fluid through a tube. This is often carried out using a valve. However, valves can be expensive, and have a number of parts, making the valve susceptible to wear and eventual failure. On the other hand, there are instances, e.g., using flexible tubing, where the tube material itself can act as a valve, such as by "pinching off" a hollow section defined by the inner diameter of the tube.

According to aspects of the present disclosure, a tube holder is disclosed that includes a tube clamp. The tube clamp is operated to selectively pinch a flexible tube held thereby, thus closing off a hollow section of the tube to prevent fluid from flowing through a pinch point of the tube. Certain embodiments include a tube holder for a single tube. Other embodiments facilitate holding any number of tubes in various configurations, e.g., parallel, in a common plane, etc. This can be accomplished by aggregating a set of independent tube clamps, or by including a set of tube clamps in a common housing. For instance, some embodiments provide a common tube holder that contains one or more tube clamps. In other embodiments, combinations of tube clamps are provided together, where each individual tube clamp can selectively clamp one or more tubes.

Moreover, certain aspects herein provide a locking mechanism that can be used to lock a tube clamp (or tube clamps) to prevent access thereto. The ability to lock a tube clamp can find numerous applications. For instance, in the medical field, the ability to lock a tube clamp except when accessed by medical professional can aid in the prevention of in-hospital and outpatient intravenous drug overdoses, e.g., in patients receiving ongoing intravenous therapies. Also, industrial and commercial applications exist, e.g., where it is desirable to prevent unauthorized access to tube ports.

Tube Lock

Figure 1:
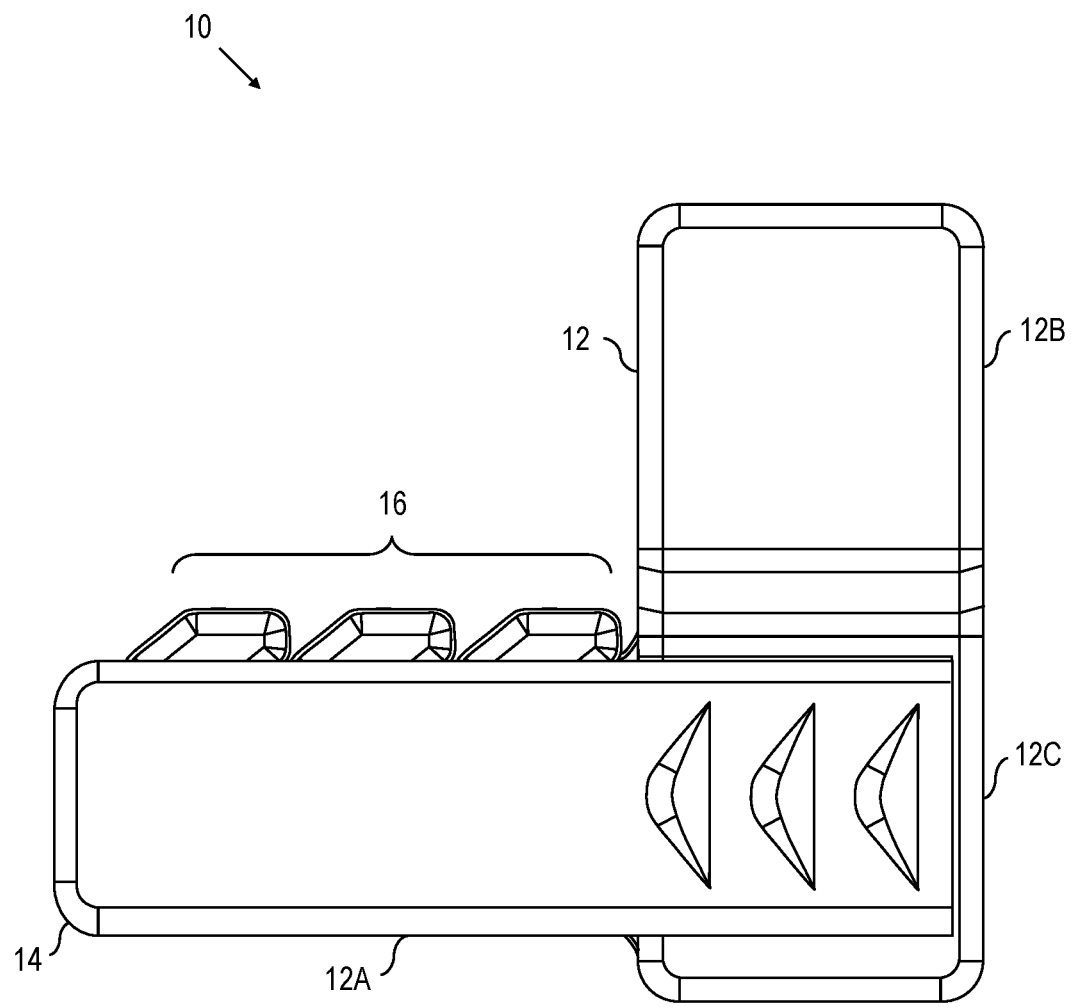
FIG. 1 is a top view of a tube lock with a tube clamp, according to aspects of the present disclosure herein.
Figure 2:
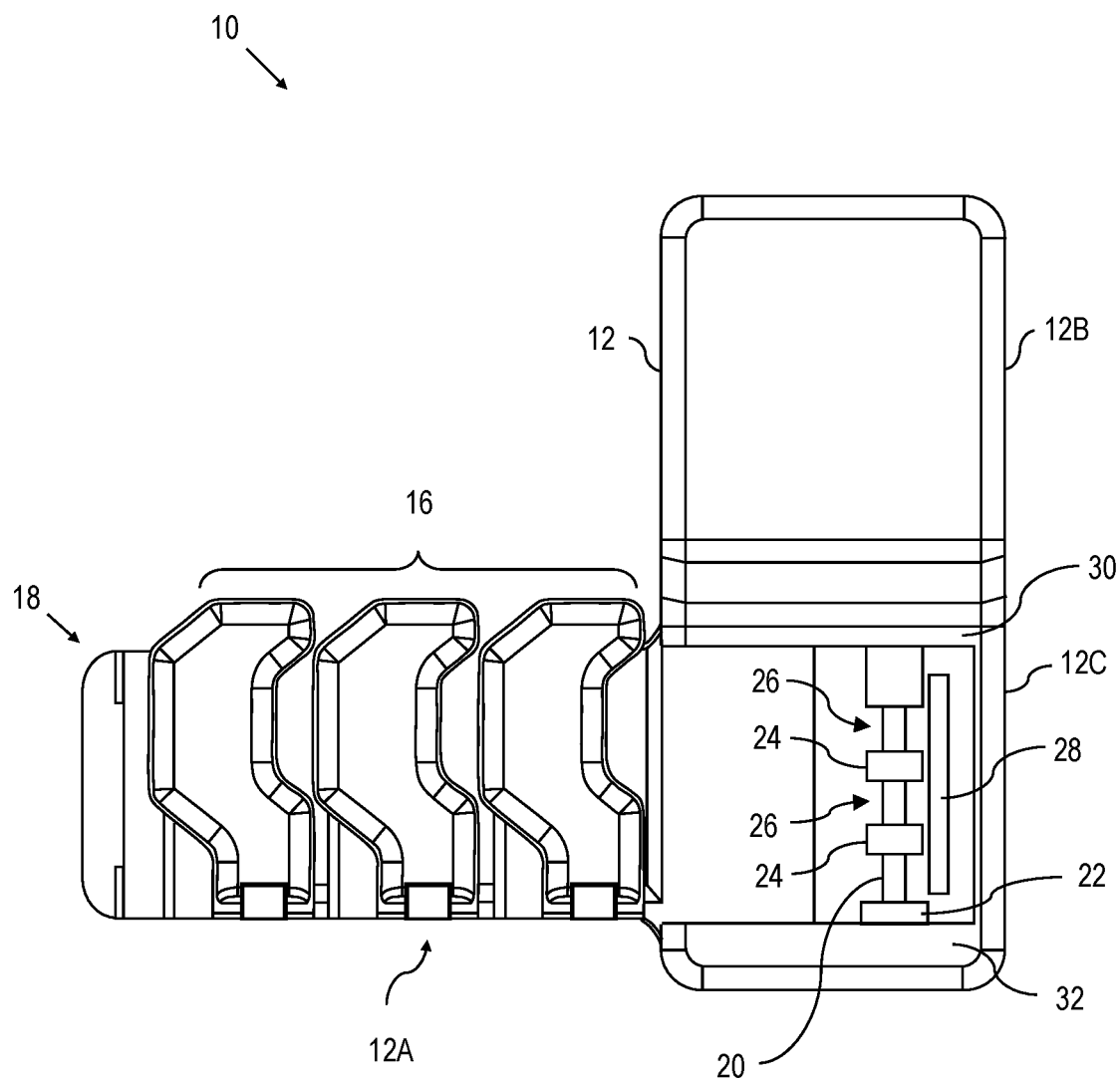
FIG. 2 is a top view of the tube lock illustrated in FIG. 1, having a clamp cover removed to expose tube clamps, according to aspects of the present disclosure.

Referring now to the drawings, and in particular to FIG. 1 and FIG. 2, a tube lock 10 is illustrated according to aspects of the present disclosure herein. FIG. 1 and FIG. 2 are both top down views, but a cover seen in FIG. 1 is removed in FIG. 2 to illustrate aspects of the present disclosure. The tube lock 10 refers generally to the combination of both a tube clamp and a locking mechanism, both of which are described in greater detail herein.

In general, the tube lock 10 includes a lock housing 12, a clamp cover 14 (FIG. 1), and can include an optional tube clamp 16.

The lock housing 12 can have one or more compartments therein. For instance, the illustrated lock housing includes a tube clamp compartment 12A. The tube clamp compartment 12A holds at least one tube clamp 16 as described more fully herein with regard to FIG. 9-FIG. 17. Moreover, the tube clamp compartment 12A has a clamp compartment opening 18 (FIG. 2) therein. The clamp compartment opening 18 provides a convenient means to access tubes that are clamped in the tube clamp 16 when the tube clamp 16 is within the clamp compartment 12A. Normally, the clamp cover 14 mates with the lock housing 12 (FIG. 1) to provide a barrier over the clamp compartment opening 18 (FIG. 2), thus restricting access to the tube clamp 16. Correspondingly, opening the clamp cover 14 provides access to the tube clamp 16.

The lock housing 12 can also include a control compartment 12B. The control compartment 12B is utilized to store optional control components, such as electronics, an actuator, a power source, etc., as will be described in greater detail herein. In some embodiments, the control compartment 12B can include an optional cover or other access. Such may be provided where a replaceable power source such as a battery is provided. In this regard, the control compartment 12B can be bifurcated or otherwise divided into user accessible areas (e.g., battery compartment), and non-user accessible areas (e.g., lock control electronics). In other applications, e.g., a purely mechanical locking/unlocking system, where an energy storage device is wirelessly or otherwise remotely charged or energized to provide power to electronics, where an energy source (e.g., a battery) is not user replaceable, etc., the control compartment 12B can be sealed and have no end-user access. The control compartment 12B and the contents thereof, are discussed in greater detail herein.

The lock housing 12 may further comprise a lock compartment 12C. The lock compartment 12C includes the structures provided to lock the clamp cover 14 to the lock housing 12. In this regard, when the clamp cover 14 is locked, a user cannot gain access to the tube clamp 16. Thus, security is provided. On the other hand, a user having privileges, including the necessary key and/or credentials can unlock the clamp cover 14 and open the clamp cover 14 to expose the clamp compartment opening 18, thus gaining access to the tube clamp 16 and hence, tubes therein.

Referring briefly to FIG. 2, in an example embodiment, the lock compartment 12C includes a cover lock 20. The cover lock 20 is controlled to transition between a locked state and an unlocked state, thus enabling the clamp cover 14 to transition between an open (unlocked) position and a closed (locked) position. Thus, in some embodiments, e.g., where a lock is provided, the cover lock 20 is configured to lock the clamp cover 14 to the lock housing 12 when the cover lock 20 is in the locked state.

For instance, the illustrated cover lock 20 includes a shaft that terminates in a shaft support 22. One or more shaft locks 24 are positioned along a length of the cover lock 20, where adjacent shaft locks 24 are spaced by release regions 26. An optional cover support 28 can be used, for instance, adjacent to the cover lock 20, to provide a support structure for the clamp cover 14.

Yet further, the lock compartment 12C includes a first cover hinge slide channel 30 and a second cover hinge slide channel 32. As will be described in greater detail below, the first cover hinge slide channel 30 and the second cover hinge slide channel 32 enable the clamp cover 14 to slide across the lock housing 12 in a lateral direction across at least a portion of the tube clamp compartment 12A sufficient to facilitate unlocking the tube lock 10, and opening the clamp cover 14.

From a manufacturing perspective, the lock housing 12 can be provided as a clamshell that is welded, glued, or otherwise closed once the components have been installed therein. In other embodiments, the lock housing 12 can be assembled from one or more components, e.g., a body, bottom lid and top lid, a single piece, etc.

The illustrated tube clamp 16 is for purposes of illustration, and not by way of limitation. Thus, three tube clamps are shown solely for convenience of discussion herein; a different number of tube clamps may be used instead. In some embodiments, the tube clamp 16 is separable from the lock housing 12. For instance, when the clamp cover 14 is unlocked from the lock housing 12, the tube clamp 16 can be inserted into, and removed from the clamp compartment opening 18. In other embodiments, the tube clamp 16 is built in, fixed, integral, or otherwise not removeable from the lock housing 12. Here, a tube can be positioned within, and removed from a corresponding tube clamp 16 when the clamp cover 14 is unlocked from the lock housing 12 and the corresponding tube clamp 16 is in an unclamped/unlocked position.

Yet further, the tube clamp compartment 12A can be configured to correspond with a precise number of tube clamps, or the tube clamp compartment 12A can be sized independently of the tube clamp(s) 16 therein. This allows a single lock housing 12 to accommodate multiple variations of tube clamps 16.

The tube clamp 16 can be implemented by any combination of embodiments described with regard to FIG. 9-FIG. 17 discussed more fully herein. However, for sake of introduction, the tube clamp 16 can include one or more individual tube clamps. Generally, each tube clamp includes a housing having a tube receiving channel therethrough. In some embodiments, the housing has a tube entry along a major surface thereof, and a first tube passageway that extends from the tube entry into the housing, and couples to the first tube passageway. This allows peripheral insertion of a tube, as described more fully herein. The tube clamp 16 also includes a clamping mechanism having a lever handle user operable to transition from a first position (e.g., an unclamped/unlocked position) to a second position (e.g., a clamped/locked position). Also, a tube pinch is coupled to the lever handle. As such, when a tube is positioned within the tube receiving channel and the lever handle of the clamping mechanism is in the second position, the tube clamp pinches the tube so as to prevent a flow of a fluid through the tube. The clamping/pinching force also "locks" the tube to the tube clamp 16 preventing extraction of the tube from the tube receiving channel. Moreover, when the clamp cover 14 is mated with the lock housing 12, the lever handle of the clamping mechanism is prevented from transitioning from the second position to the first position, thus locking the tube inserted into the tube clamp.

In some embodiments, the tube lock 10 is provided with a tube clamp 16. In other embodiments, e.g., where a tube clamp 16 is separable from the tube lock 10, the tube lock 10 need not include a tube clamp 16 therewith. As such, in some embodiments, a tube lock 10 can comprise a lock housing 12 comprising a tube clamp compartment 12A having a clamp compartment opening 18 therein. A clamp cover 14 mates with the lock housing 12 to provide a barrier over the clamp compartment opening 18 such that when a tube clamp 16 having a lever handle is inserted into the clamp compartment and the clamp cover 14 is mated with the lock housing 12, the lever handle is prevented from lifting sufficient to peripherally release a tube held by the tube clamp. In some embodiments, the lever handle is prevented from lifting a sufficient amount to release the clamping/pinching force that prevents fluid flow. As such, fluid flow through the pinch point created by the tube clamp is positively prevented when the tube clamp 16 is in the tube lock 10 and the clamp cover 14 is mated with the lock housing 12.

Cover Latching

Figure 3:
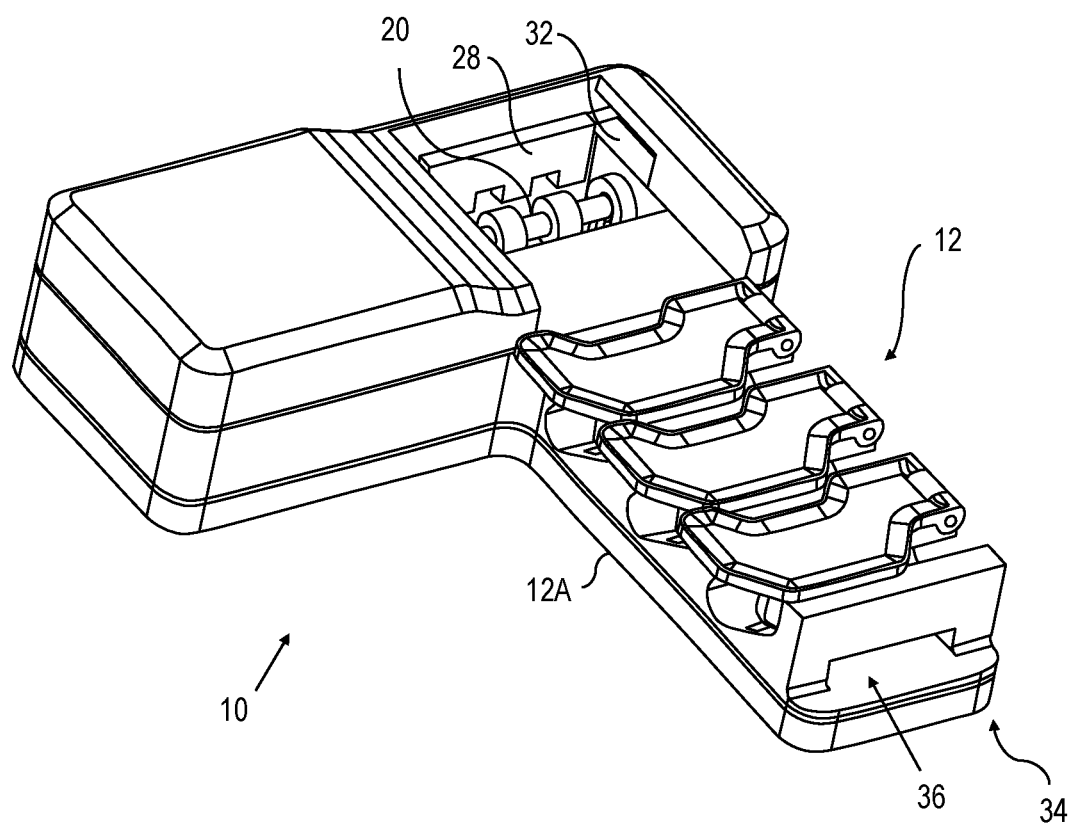
FIG. 3 is a perspective view of the tube lock illustrated in FIG. 1, having a clamp cover removed to expose tube clamps, according to aspects of the present disclosure.

Referring to FIG. 3, in an example embodiment, the tube clamp compartment 12A has a distal end 34 having a cover slot 36 therein.

Clamp Cover

Figure 4:
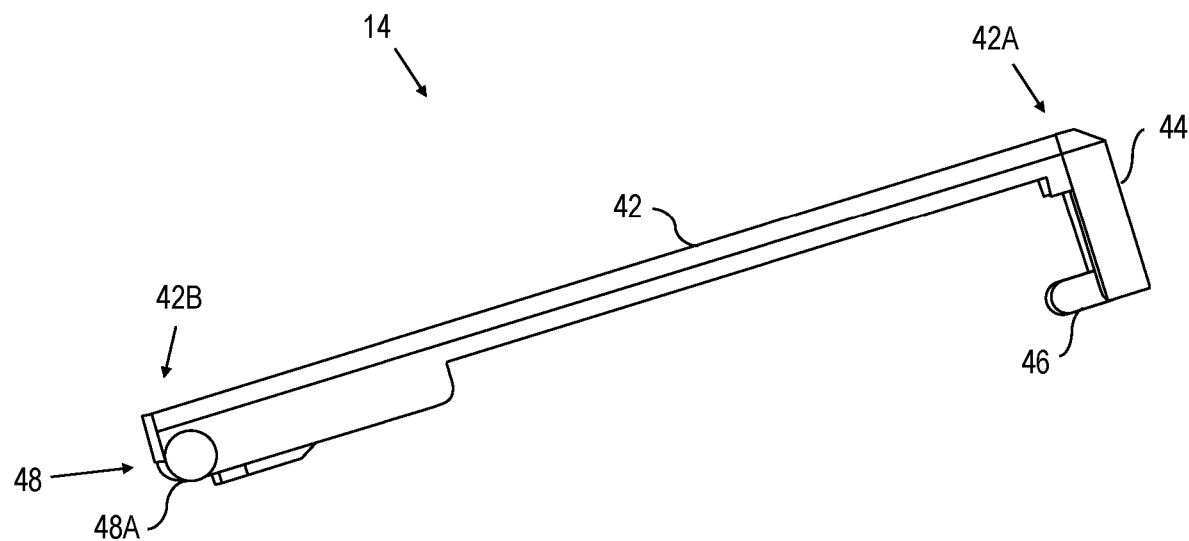
FIG. 4 is a side view of a clamp cover for a tube lock.
Figure 5:
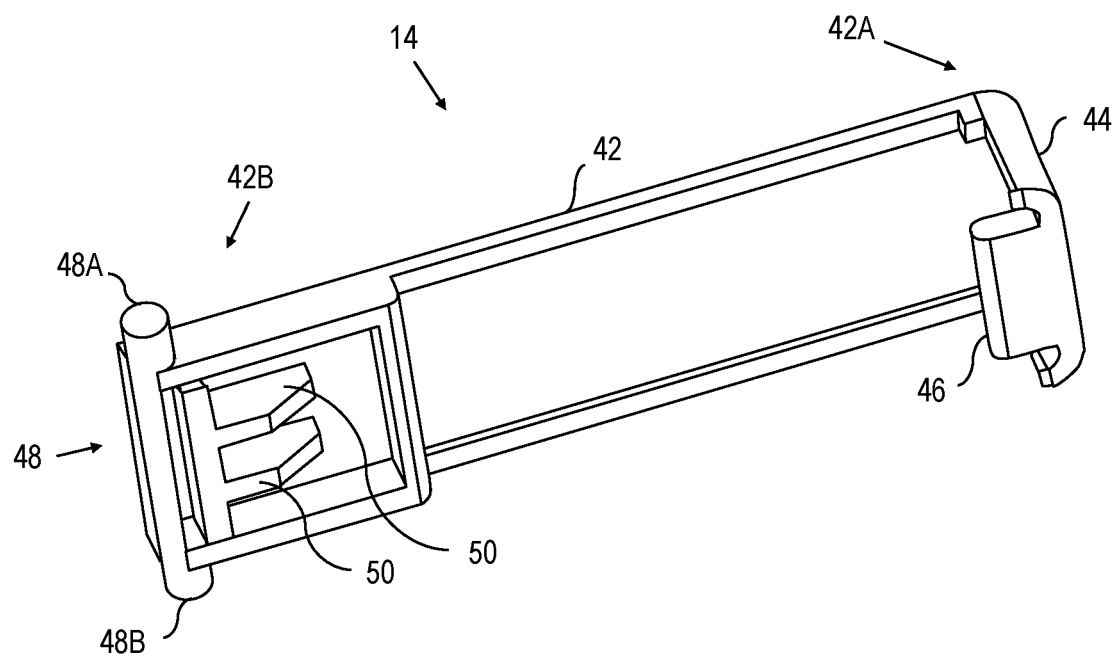
FIG. 5 is a perspective view of the clamp cover of FIG. 4.

Referring to FIG. 4 and FIG. 5, the clamp cover 14 includes a lid portion 42 having a first end 42A and a second end 42B. The clamp cover 14 also includes a side portion 44. As illustrated, the side portion extends generally orthogonally from the first end 42A of the lid portion 42. The side portion 44 includes an overbite 46 extending therefrom. The overbite 46 is configured to correspond to the cover slot 36 (FIG. 3) provided on the distal end 34 of the tube clamp compartment 12A. Also as illustrated, the clamp cover 14 includes a hinge component 48 positioned generally proximate to the second end 42B of the lid portion 42. The hinge component 48 includes a first hinge end 48A and a second hinge end 48B, e.g., implemented as rod ends or pins as illustrated. Other configurations can be implemented in lieu of rod shaped ends.

Referring to FIG. 1-FIG. 5, when the clamp cover 14 is in a locked position relative to the lock housing 12, the overbite 46 of the clamp cover 14 is seated in the cover slot 36 of the lock housing 12 (in the tube clamp compartment 12A of the lock housing 12 as illustrated). Moreover, the hinge component 48 of the clamp cover 14 seats in a set of channels defined by the first cover hinge slide channel 30 and the second cover hinge slide channel 32. The first hinge end 48A of the hinge component 48 engages the first cover hinge slide channel 30 and the second hinge end 48B of the hinge component 48 engages the second cover hinge slide channel 32. When the clamp cover 14 is locked, the clamp cover 14 is prevented from sliding in the set of channels, thus prohibiting the overbite 46 from releasing from the cover slot 36.

On the other hand, when the clamp cover 14 is unlocked, the hinge component 48 can slide in the set of channels such that the clamp cover 14 can slide laterally towards the tube clamp compartment 12A. That is, when the clamp cover 14 is unlocked, the first cover hinge slide channel 30 and the second cover hinge slide channel 32 enable the clamp cover 14 to slide laterally across the tube clamp compartment 12A of the lock housing 12, thus pushing the overbite 46 out from the cover slot 36.

Referring specifically to FIG. 5, the clamp cover 14 also includes one or more lock wedges 50. The lock wedges 50 cooperate with the shaft locks 24 to lock the clamp cover 14, as described more fully herein.

Cover Lock Key

In some embodiments, the clamp cover 14 is opened by a physical key or special tool. In other embodiments, the clamp cover 14 is opened electronically.

Cover Lock Control

Figure 6:
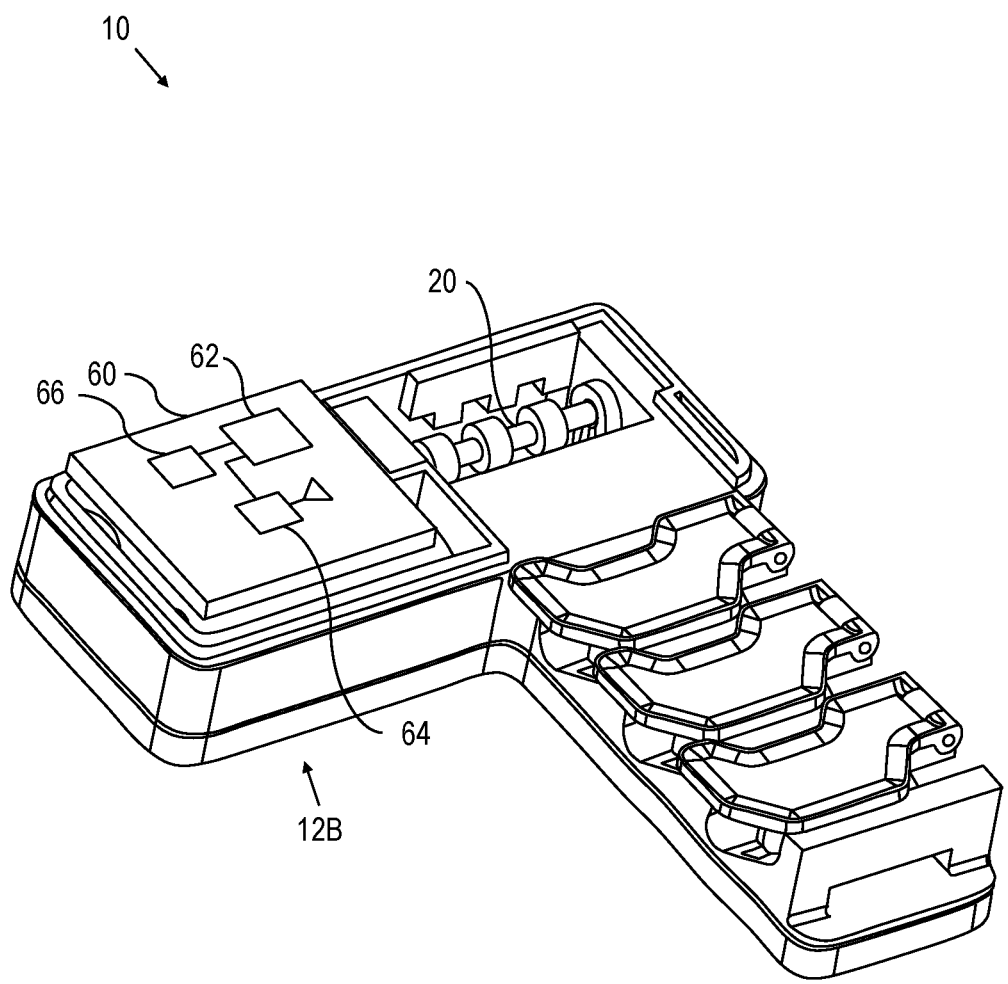
FIG. 6 is a perspective view of the tube lock illustrated in FIG. 1, having a clamp cover removed to expose tube clamps, and a portion of a housing removed to expose electronics to control a cover lock, according to aspects of the present disclosure.

Referring to FIG. 6 the control compartment 12B can include the necessary electronics 60 that electronically control the cover lock 20 (FIG. 2). For instance, in the illustrated example embodiment, the electronics 60 can comprise a controller 62 communicably coupled to the cover lock 20 (e.g., via an electromechanical device such as an actuator, motor, etc.). The electronics can also include a wireless device 64 that is communicably coupled to the controller 62. Under this configuration, the controller 62 is configured to transition the cover lock 20 from the locked state to the unlocked state, e.g., responsive to an unlock command received from the wireless device. Here, the unlock command is wirelessly received by the wireless device 64.

By way of illustration, the wireless device 64 can comprise a near field communication (NFC) device, Radio Frequency Identification (RFID) device, etc.

In some embodiments, the wireless device 64 can also and/or alternatively include any combination of a Bluetooth device, ultra-wideband (UWB) device, Zigbee device, cellular device, Wi-Fi device, combinations thereof, etc., which can be configured as, or coupled to, a receiver, transmitter, or transceiver.

For technologies such as NFC or RFID, the wireless device 64 is configured to respond to a corresponding unlock device, e.g., a remote tag. In practical applications, the remote tag can be implemented as a chip, badge, NFC-enabled or RFID-enabled smartphone, RFID keyfob, external pushbutton, special purpose electronic key device, or other suitable remote device that is configured to transmit or otherwise provide a unique code or other authentication information to the wireless device 64. The wireless device 64, the controller 62, or other suitable processor provided in the electronics 60 can optionally provide any necessary encoding, conversion, authentication, etc.

For technology such as Bluetooth, ultra-wideband, cellular, Zigbee, Wi-Fi, etc., the remote device may be a dedicated appliance, smart phone, tablet, laptop, computer, etc.

As another example, using NFC or RFID, energy harvesting and/or onboard power can be used to implement unlocking functionality. In such embodiments, there is no (or low) onboard energy storage. Rather, a corresponding unlock device houses the power needed to unlock the clamp cover 14. As such, when there is no unlock device present, the NFC or RFID mechanism is simply doing nothing. However, an NFC-enabled and/or RFID-enabled unlock device can be brought into sufficient proximity that an antenna of the unlock device communicably couples to an antenna of the wireless device 64 for transmitting both power and signal wirelessly. This may require that that the unlock device is brought within a few meters of the housing 12 (RFID) or may even require even closer proximity (e.g., 10 centimeters or less) with NFC.

Regardless, the unlock device emits a signal that is received by an internal antenna, e.g., associated with the wireless device 64. The internal antenna and associated NFC/RFID-enabled electronics energizes and activates the controller 62. The reader passes a verified unlock signal to the controller 62, and the controller operates an actuator (e.g., which may also be powered by energy harvesting and/or onboard power) to drive the cover lock 20 to the unlocked state.

The electronics 60 can also include memory 66 communicably coupled to the controller 62. Here, the controller 62 can be operatively configured to store in the memory 66, an identifier of an operator that unlocks the tube lock 10 by reading an identifier code in a communication received by the wireless device 64. The memory 66 can also be used to store other information, such as time, date, history information, etc.

Figure 7:
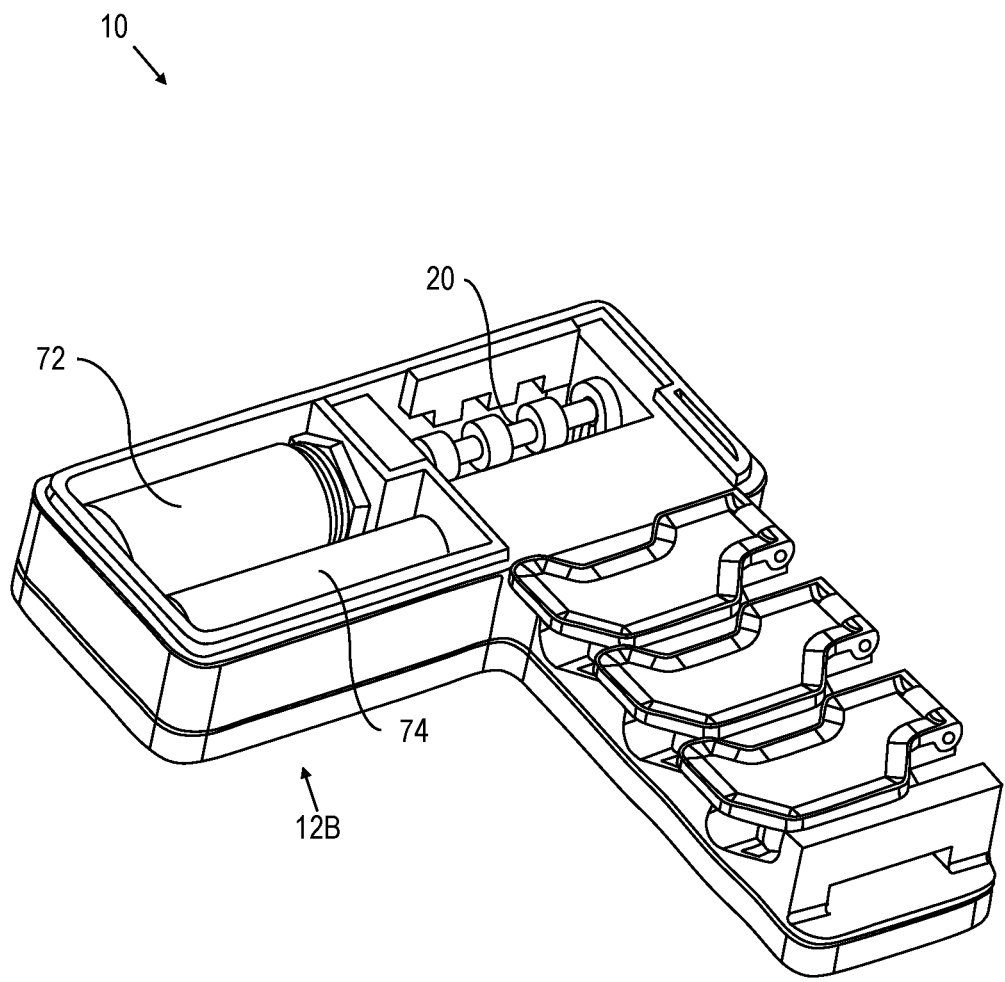
FIG. 7 is a perspective view of the tube clamp with locking mechanism illustrated in FIG. 1, having a clamp cover removed to expose tube clamps and a portion of a housing removed to expose additional components to control a cover lock, according to aspects of the present disclosure.

Referring to FIG. 7 the control compartment 12B can also include the necessary hardware to perform controlled locking functionality. For instance, the control compartment 12B in FIG. 7 is illustrated with the electronics 60 (FIG. 6) removed for clarity. Notably, the control compartment 12B includes a linear actuator 72 that is coupled to the cover lock 20. The linear actuator 72 is electrically connected to, and controlled by the controller 62 (FIG. 6).

The control compartment 12B can also contain a power source 74. The power source 74 is beneficial for embodiments where the lock itself is looking for the correct tag (which can be non-powered) to be brought within proximity so that the clamp cover 14 can be unlocked or locked. Here, control is exercised over how much power is drawn by setting the distance the wireless device 64 looks (how strong a signal the wireless device 64 emits) and how often the wireless device 64 looks (taking into account how quickly users "badge" in). Practically, this may mean a badge/tag is brought near, even physically touching the housing 12, e.g. depending upon power. Moreover, a badge/tag may be required to be held in position for a set amount of time, e.g., for up to 1 second.

In some embodiments, the power source 74 is a battery. Where user-replaceable batteries are used, the battery can be placed in a user-accessible region of the control compartment, which is isolated from the electronics 60. In other applications, the battery can be replaced by a capacitor or other charge storing device. Here, signals can be conveyed to the tube lock 10 inductively or wirelessly so that the electronics "wake up" or "energize" when the proper source (e.g., RFID-enabled device) is brought within a suitable range of the control compartment 12B.

As such, in other applications, a power source 74 is not required, e.g., where the lock is mechanical, where an antenna within the lock housing 12 wirelessly receives power, etc.

Cover Locking and Unlocking

Referring to FIG. 1-FIG. 8 generally, to unlock the clamp cover 14 from the lock housing 12, the linear actuator 72 is commanded by the controller 62 to linearly transition the shaft to an "avoidance position" where the shaft lock(s) 24 misalign with the wedge(s) 50 on the bottom side of the clamp cover 14. Here, the wedge(s) 50 align with corresponding release regions 26 along the shaft. By misaligning the shaft locks 24 with the wedges 50, a user can manually slide the clamp cover 14 laterally across the lock housing 12 towards the distal end 34 of the tube clamp compartment 12A, thus releasing the overbite 46 from the cover slot 36. The movement of the linear actuator 72 can be minor, e.g., ⅛" of an inch (approximately 3 millimeters).

Correspondingly, to lock the clamp cover 14 to the lock housing 12, the linear actuator 72 linearly moves the shaft of the cover lock 20 such that the shaft lock(s) 24 align with the wedge(s) 50. With at least one shaft lock 24 laterally in an interference position with a corresponding wedge 50, an attempt by a user to laterally shift the clamp cover 14 towards the tube clamp compartment 12A engages a physical interference preventing further lateral movement of the clamp cover 14. Notably, since the wedges 50 do not normally directly interfere with the movement of the linear actuator 72, there is no stress normally placed on the linear actuator moving the shaft to reposition the shaft lock(s) 24 between locked and unlocked states.

Figure 8:
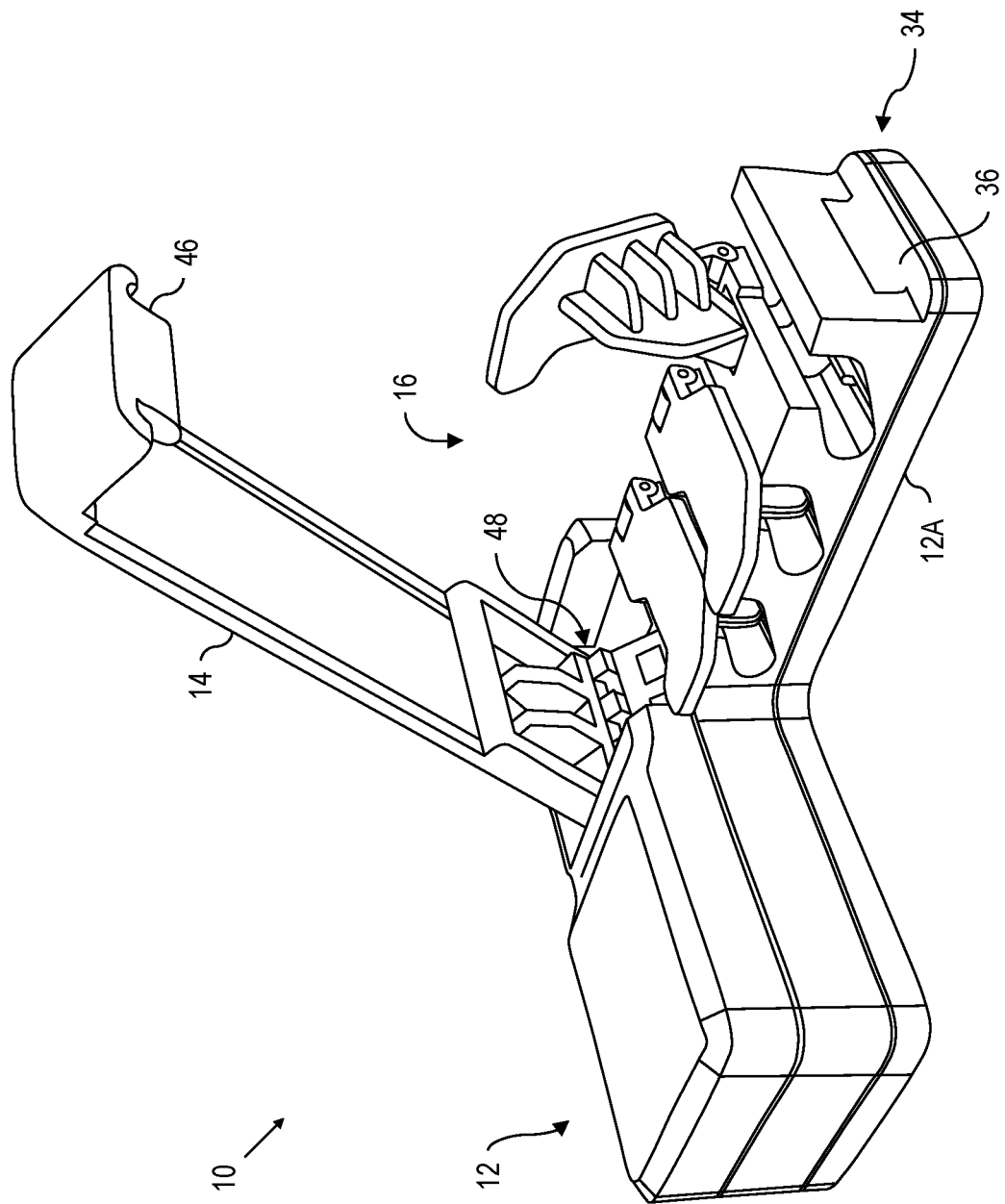
FIG. 8 is a perspective view of the tube clamp with locking mechanism illustrated in FIG. 1, with the cover in an opened, unlocked position, according to aspects of the present disclosure.

With specific reference to FIG. 8, the lock housing 12 is illustrated with the clamp cover 14 is an open position exposing the tube clamp 16 (actually, three tube clamps for sake of illustration). As illustrated, the overbite 46 was released from the cover slot 36 in the tube clamp compartment 12A via lateral sliding movement of the clamp cover 14, and the hinge component 48 is used to pivot/hinge the clamp cover 14 to an open position, enabling access to the tube clamp(s) 16.

Although illustrated as a linear actuator 72 for sake of clarity of discussion, other electro-mechanical devices could alternatively be utilized, e.g., depending upon the configuration of the lock housing 12 and clamp cover 14.

Tube Clamp

Figure 9:
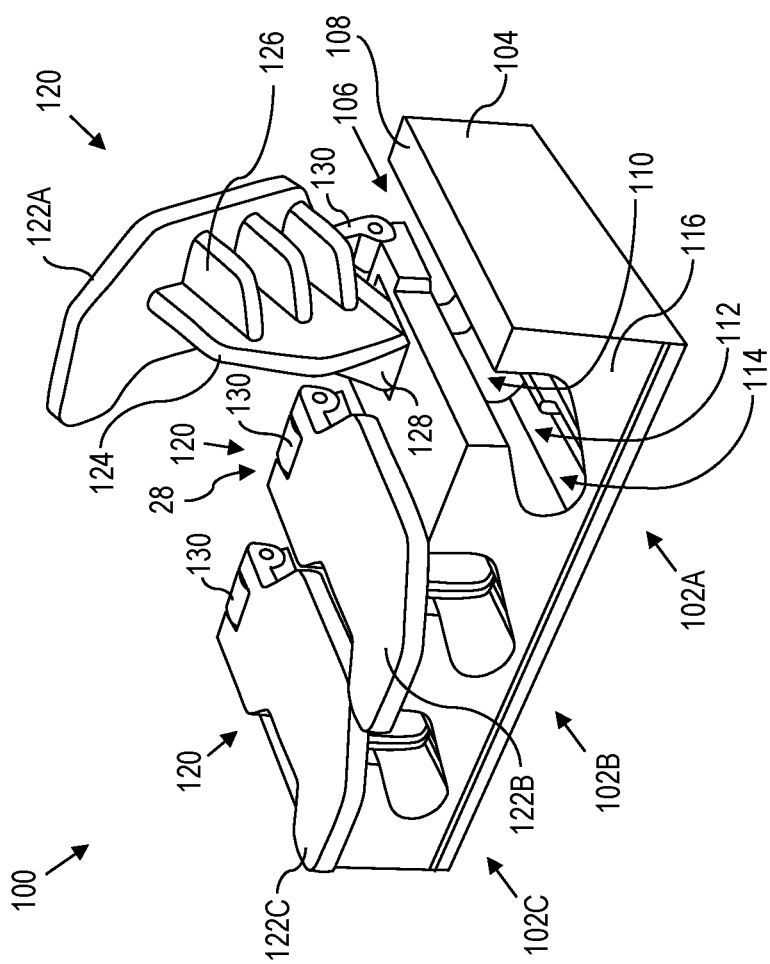
FIG. 9 is a perspective view of an example tube holder, according to aspects of the present disclosure herein.
Figure 10:
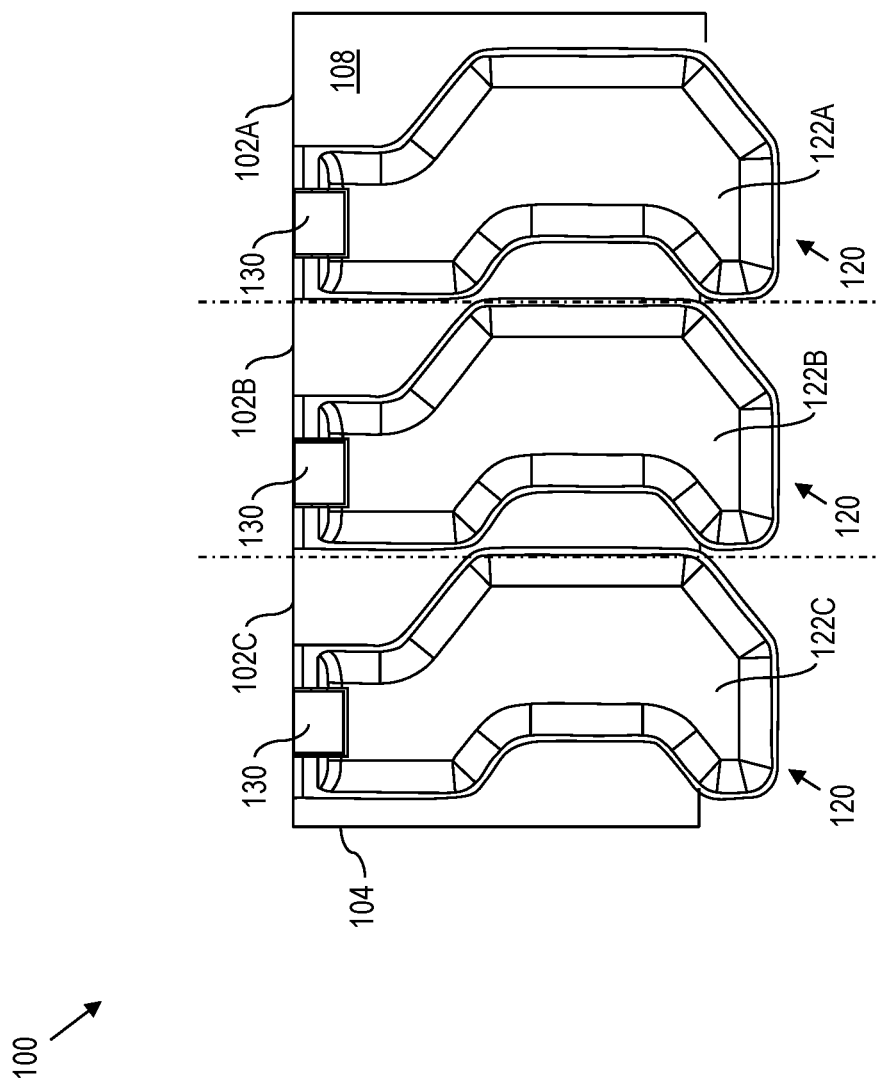
FIG. 10 is a top view of the tube holder of FIG. 9.

Referring to drawings and in particular to FIG. 9 and FIG. 10, a tube holder 100 is illustrated according to aspects of the present disclosure. The tube holder 100 can implement the tube holder 16 (FIGS. 1-8) described herein. However, the tube holder 100 is shown independent of a corresponding lock housing 12 (FIGS. 1-8) for clarity of discussion. In practical applications, the tube holder 100 can be integral with the lock housing 12 of FIG. 1-FIG. 8, or the tube holder 100 can be placed in, and removed from the lock housing 12 as noted above.

The tube holder 100 includes at least one tube clamp 102. In the illustrated embodiment, three tube clamps 102A-C (collectively 102) are illustrated solely for the convenience of illustration. As such, the tube clamps 102 are labeled tube clamp 102A for the rightmost position, tube clamp 102B for the middle position, and tube clamp 102C for the leftmost position. In practice, the tube holder 100 can include one tube clamp 102, or multiple (e.g., a set of) tube clamps 102.

In this regard, tube clamp 102A, tube clamp 102B, and tube clamp 102C are identical, unless otherwise noted.

Each tube clamp 102 has a housing 104. In practice, each tube clamp 102 can have its own housing 104, e.g., tube clamp 102A can be contained in a housing 104 that is separable from the housing 104 of tube clamp 102B, etc. Alternatively, two or more tube clamps 102 can share a common housing 104. For instance, as illustrated, tube clamp 102A, tube clamp 102B, and tube clamp 102C are all contained in a common housing 104. In some embodiments, each tube clamp 102 is in a separate housing 104, and a tray or other structure is provided to snap, assemble, align, fasten, hold, or otherwise position multiple tube clamps 102 together.

Referring specifically to FIG. 9, in the illustrated embodiment, each tube clamp 102 has a housing 104 having a tube entry 106 along a major surface 108 of the housing 104. A first tube passageway 110 extends from the tube entry 106 into the housing 104. An optional second tube passageway 112 couples to the first tube passageway 110. Moreover, a tube receiving channel 114 is coupled to the first tube passageway 110. Notably, in some embodiments, the tube receiving channel 114 can couple/connect directly to the first tube passageway 110. In other embodiments, such as that shown in FIG. 9, the tube receiving channel 114 couples to the first tube passageway 110 via one or more connecting passageways, such as the second tube passageway 112, as shown.

Notably, in the illustrated embodiment, the tube entry 106 extends across the entire major surface 108 of the housing 104. Similarly, the first tube passageway 110 defines a first passthrough that slots through the housing 104 from a front face 116 through to a back face 118. In the illustrated embodiment, the front face 116 and back face 118 define surfaces that are adjacent to the major surface 108. In particular, the front face 116 and the back face 118 are each orthogonal to the major surface 108, and are generally parallel to each other. However, in other embodiments, the front face 116 and the back face 118 need not be parallel to each other.

Moreover, as illustrated, the first tube passageway 110 extends from the tube entry 106 into the housing 104 in a direction perpendicular to the major surface 108, e.g., straight down into the housing 104. However, in other embodiments, the first tube passageway 110 can extend into the housing at other angles. Moreover, the optional second tube passageway 112 connects the first tube passageway 110 to the tube receiving channel 114 such that the second tube passageway 112 extends angularly into the housing 104 from the first tube passageway 110 (and connecting to the tube receiving channel 114). Moreover, in the example embodiment, the second tube passageway 112 defines a second passthrough that slots through the housing 104 from the front face 116 through to the back face 118. In this regard, the first tube passageway 110, the second tube passageway 112, and the tube receiving channel 114 form a "sock shape" profile on the front face 116 of the housing 104. By "slotting through" the housing 104, a tube can be peripherally inserted into the tube receiving channel 114. Peripheral insertion allows an axial length of the tube to be draped across the tube entry 106, and dropped down into the tube receiving channel 114. As such, there is no requirement that a tube tip/tube end is pushed through the housing 104. This can provide significant advantages, such as where a tube includes an adapter, head, port, or other device on an end thereof.

Notably, the tube entry 106, first tube passageway 110, second tube passageway 112, or combination thereof, enable peripheral insertion of a tube (e.g., inserting the tube into the tube holder by sliding a portion of the tube body/length into the tube holder 100 without axially pushing a tip of the tube through the housing 104). This approach makes the tube holder 100 compatible with applications that have/require fittings on the tube (e.g., some PICC-lines (Peripherally Inserted Central Catheter) or other medical tubes, some tubes with permanently installed connectors, etc.)

In alternative embodiments (e.g., where peripheral insertion is not a requirement because there are no fittings or other limitations on the tip of the tube), the housing 104 need not include the tube entry 106, first tube passageway 110, second tube passageway 112, or combination thereof. Rather, the tube receiving channel 114 can tunnel through the housing 104 via a hole/passageway that extends from the front face 116 through to the back face 118. This configuration allows a tube to be inserted into the tube housing 104 via a tip/end of the tube. The tube could then be slid along its length to a point where clamping is desired.

Referring generally to FIG. 9 and FIG. 10, each tube clamp 102 also includes a clamping mechanism 120. The clamping mechanism 120 includes a lever handle 122 that is user operable to transition from a first position (e.g., an unclamped/unlocked position) to a second position (e.g., a clamped/locked position). For instance, since there are three tube clamps 102A, 102B, 102C illustrated for sake of clarity, tube clamp 102A includes a lever handle 122A, tube clamp 102B includes a lever handle 122B, and tube clamp 102C includes a lever handle 122C. In FIG. 9, lever handle 122A is illustrated as being in the first position. Lever handle 122B and lever handle 122C are each illustrated in the second position. Comparatively, in FIG. 10, each lever handle 122 is in the second position.

Referring back to FIG. 9, and in particular, to the perspective view of the lever handle 122A, a gate 124 is coupled to the lever handle 122. In this regard, the gate 124 can include optional wings 126, which can provide reinforcement, etc. Additionally, a tube pinch 128 is coupled to the lever handle 122. Accordingly, when the lever handle 122 is in the second position (see for example lever handle 122B, and lever handle 122C), the gate 124 at least partially blocks the tube receiving channel 114 from the first tube passageway 110 (and in some embodiments, the gate 124 also at least partially blocks the tube receiving channel 114 from the second tube passageway 112). Yet further, in embodiments where there is no tube entry 106, first tube passageway 110, second tube passageway 112, etc., the gate is not provided.

Regardless of whether or not a gate 124 is provided, when the lever handle 122 is in the second position (see for example lever handle 122B, and lever handle 122C), the tube pinch 128 is disposed in a "clamped position" relative to the tube receiving channel 114. The "clamped position" is a position that pinches a flexible tube installed/positioned within the tube receiving channel 114 by an amount that is sufficient to prevent the flow of fluid through the tube at the pinch point created by the tube pinch 128 cooperating with the tube receiving channel 114. In certain embodiments, this pinching/clamping force also "locks" the tube to the tube clamp, e.g., such that the tube cannot readily be extracted from the tube receiving channel.

In some embodiments, the clamping mechanism 120 is further configured such that when the lever handle 122 is in the second position, the lever handle 122 at least partially covers the tube entry 106. This is most closely seen with regard to lever handle 122B and lever handle 122C.

As such, in some embodiments when a tube is peripherally inserted so as to drop from the tube entry 106 through the first tube passageway 110 and into the tube receiving channel 114, and the lever handle 122 of the clamping mechanism 120 is in the second position (e.g., see lever handle 122B, and lever handle 122C), the gate 124 prevents the tube from exiting the housing 104 via the first tube passageway 110. Moreover, the tube pinch 128 pinches the tube so as to prevent a flow of a fluid through a pinch point of the tube.

To release a tube from the tube receiving channel 114, the lever handle 122 is moved to the first position, which allows the tube to peripherally lift out of the housing from the tube receiving channel 114 (or to pull through the tube receiving channel 114, e.g., where there is no fitting on the tube that would interfere).

For instance, in some embodiments, the clamping mechanism 120 is configured such that when the lever handle 122 is in the first position (e.g., see lever handle 122A), the gate 124 exposes the tube receiving channel 114 to the first tube passageway 110 and the tube pinch 128 is disposed in an unclamped position relative to the tube receiving channel 114. Thus, a corresponding tube dropped into the tube receiving channel 114 is not pinched, and thus fluid can flow through the tube. Also, the tube can be peripherally inserted or removed from the tube holder 100.

Referring again to FIG. 9 and FIG. 10, in some embodiments, the clamping mechanism 120 is hinged via a hinge 130 so as to pivot about the first major surface 108 of the tube clamp 102. The hinge 130 allows ready transitioning of the clamping mechanism 120 between the first position to the second position (e.g., open and closed positions). In this regard, the hinge 130 can optionally include a spring or other feature to facilitate a tactile operation. An optional spring can also be used to bias the clamping mechanism 120 closed such that a tube positioned in the tube receiving channel 114 is pinched closed. In some embodiments, a "snap", "clasp", hook, click lock or other feature may be used (e.g., as part of the clamping mechanism 120 or otherwise) to ensure that when the clamping mechanism 120 is in the closed position, a tube positioned therein remains pinched closed. In this regard, the type of tube, tube flexibility, tube diameter, etc., may influence the manner in which the clamping mechanism remains closed.

In some embodiments, the tube clamp is configured to accept medical tubes. In this regard, a width of the tube entry 106 and tube receiving channel 114 (FIG. 9) are sufficient to enable insertion of the tube, where the tube is implemented as at least one of a central line catheter, an intravenous line, a PICC-line, a fluid carrying flexible tube, etc. By way of non-limiting example, a tube diameter can range from approximately 1-11 millimeters. In other applications, such as robotics, industrial, automotive, consumer, etc., the tube entry 106 (FIG. 9) was a sufficient width to accommodate the largest tube diameter that is anticipated to be used by the device.

As noted above, the clamping mechanism 120 includes a tube pinch 128 (FIG. 9) that pinches a tube peripherally inserted into the tube receiving channel 114 (FIG. 9). In this regard, in an embodiment that utilizes a hinge 130, operation of the lever handle 122 from the open to the closed position may correspondingly pivot the tube pinch 128 from a "pinch" position with the tube receiving channel to a spaced position, which may require the tube pinch 128 to travel through the housing 104.

Figure 11:
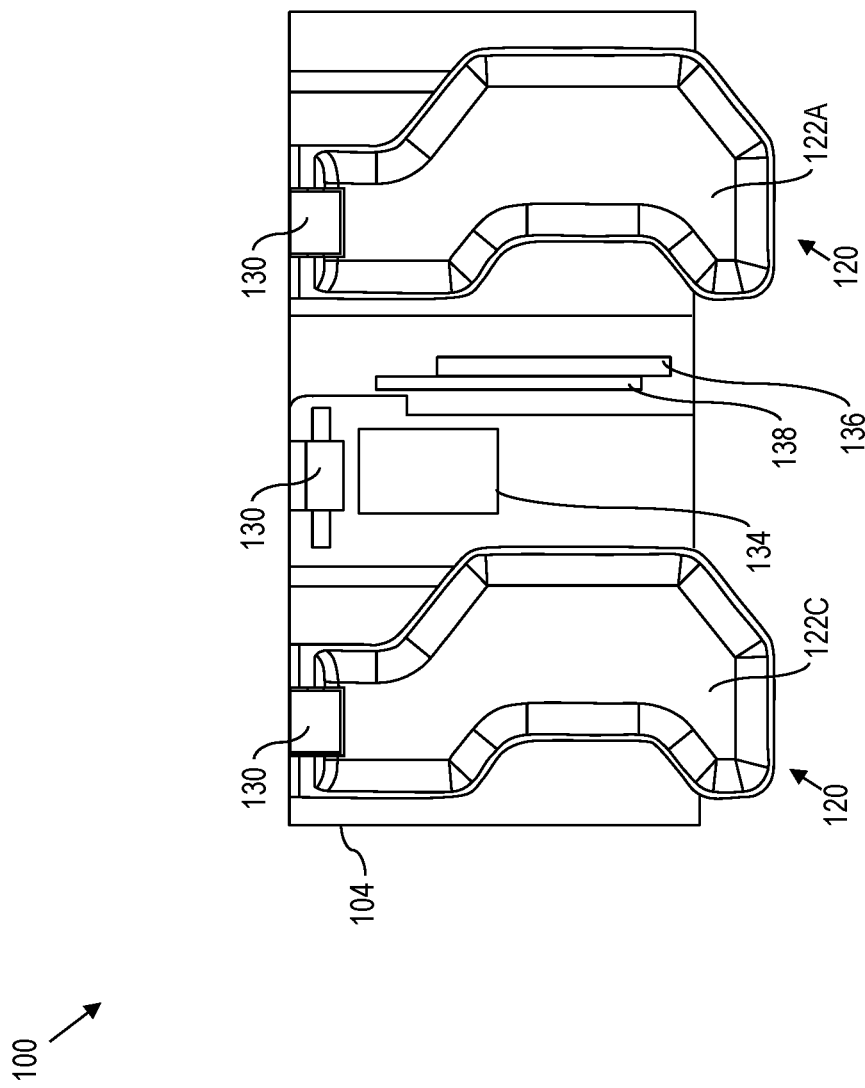
FIG. 11 is a top view of the tube holder of FIG. 9, having a lever handle removed to illustrate features of the housing, according to aspects of the present disclosure.
Figure 12:
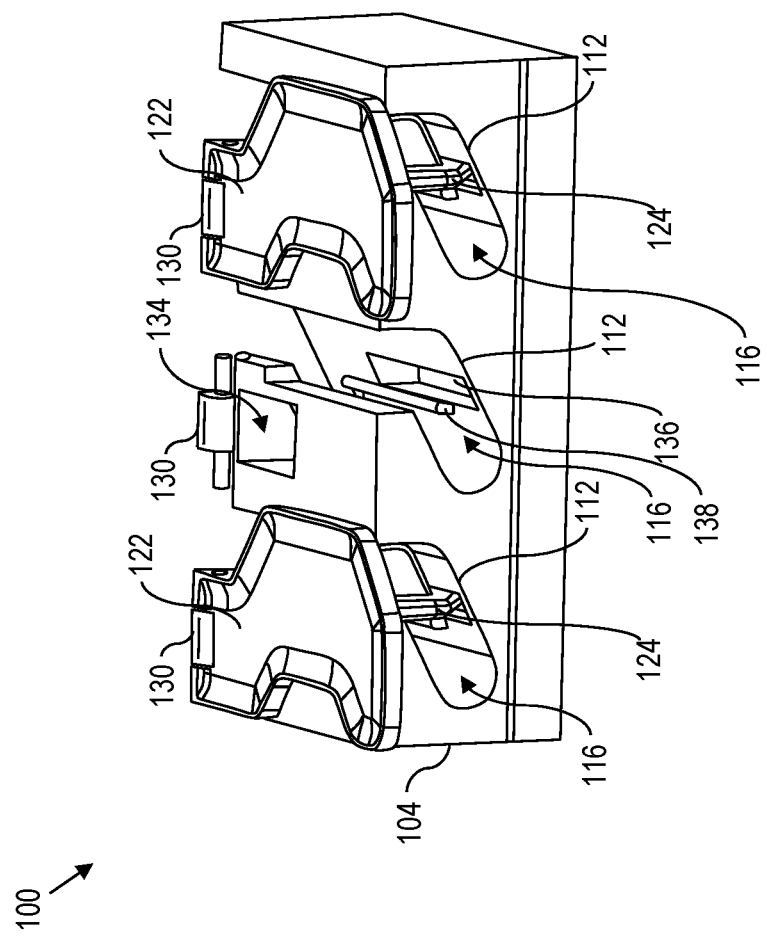
FIG. 12 is a perspective view of the tube holder of FIG. 9, having a lever handle removed to illustrate features of the housing, according to aspects of the present disclosure.
Figure 13:
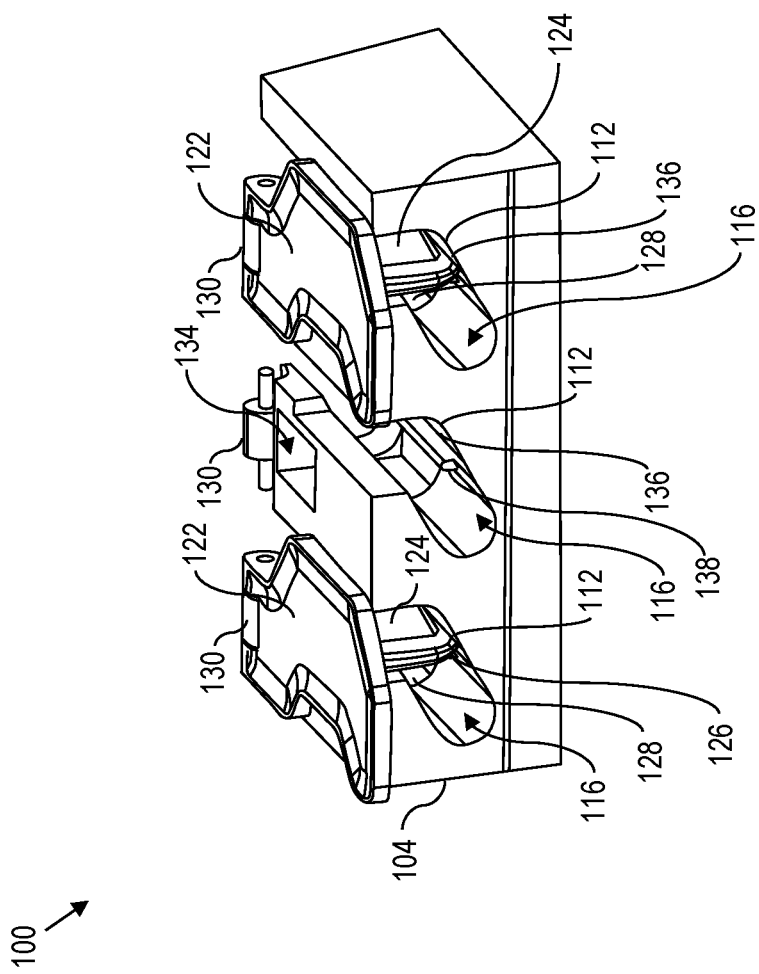
FIG. 13 is another perspective view of the tube holder of FIG. 9, having a lever handle removed to illustrate features of the housing, according to aspects of the present disclosure.

Referring to FIG. 11, FIG. 12, and FIG. 13 generally, the tube holder 100 is illustrated with the lever handle 122B (FIG. 9 and FIG. 10) removed for clarity of illustration. In this regard, FIG. 11-FIG. 13 illustrate various features of the tube holder 100 that are common, including features common with FIG. 9 and/or FIG. 10. As such, like structure is illustrated with like reference numbers and a detailed description is omitted except to clarify differences.

Notably, an aperture 134 extends through the first major surface 108 and forms a pinch passageway into the housing 104. The aperture 134 and corresponding pinch passageway allows the tube pinch 128 to transition into and out of the tube receiving channel 114 as the lever handle 122 is pivoted about the hinge 130 between open and closed positions.

In some embodiments, the housing 104 can also include a gate receiving channel 136. The gate receiving channel 136 is positioned in the second tube passageway 112 in the illustrated embodiment. However, in practice, the gate receiving channel 136, where provided, can be positioned anywhere in the housing 104 that aligns in register with the gate 124 of the clamping mechanism 120. Notably, when the handle lever 122 is in the closed position, and when a tube has been peripherally inserted into the tube receiving channel 114, at least an edge of the gate 124 sits into the gate receiving channel 136. Because the gate receiving channel 136 recesses into the housing 104 from the second tube passageway 112, the tube is physically blocked from exiting the tube holder 100. In some embodiments, the tube cannot be withdrawn from the tube receiving channel back through the second tube passageway 112 because the gate 124 cooperates with the gate receiving channel 136 to physically block the entire second tube passageway 112.

The gate 124 can also be used to ensure proper loading of the device. For instance, if a tube were to be positioned over the tube entry 106, and the lever handle 122 is transitioned from the open to the closed position, the edge of the gate 124 would push the tube peripherally down the first tube passageway 110, through the second tube passageway 112, and into the tube receiving channel 114. The gate 124 would disengage the tube as the edge of the gate 124 enters the gate receiving channel 136.

Also as illustrated, in some embodiments, each tube clamp 102 can include a barricade 138 forming a divider between the second tube passageway 112 and the tube receiving channel 114. The barricade 138 prevents a tube peripherally inserted into the tube receiving channel 114 from slipping out, e.g., during handling and until the lever handle is transitioned to the second position (closed position).

Figure 14:
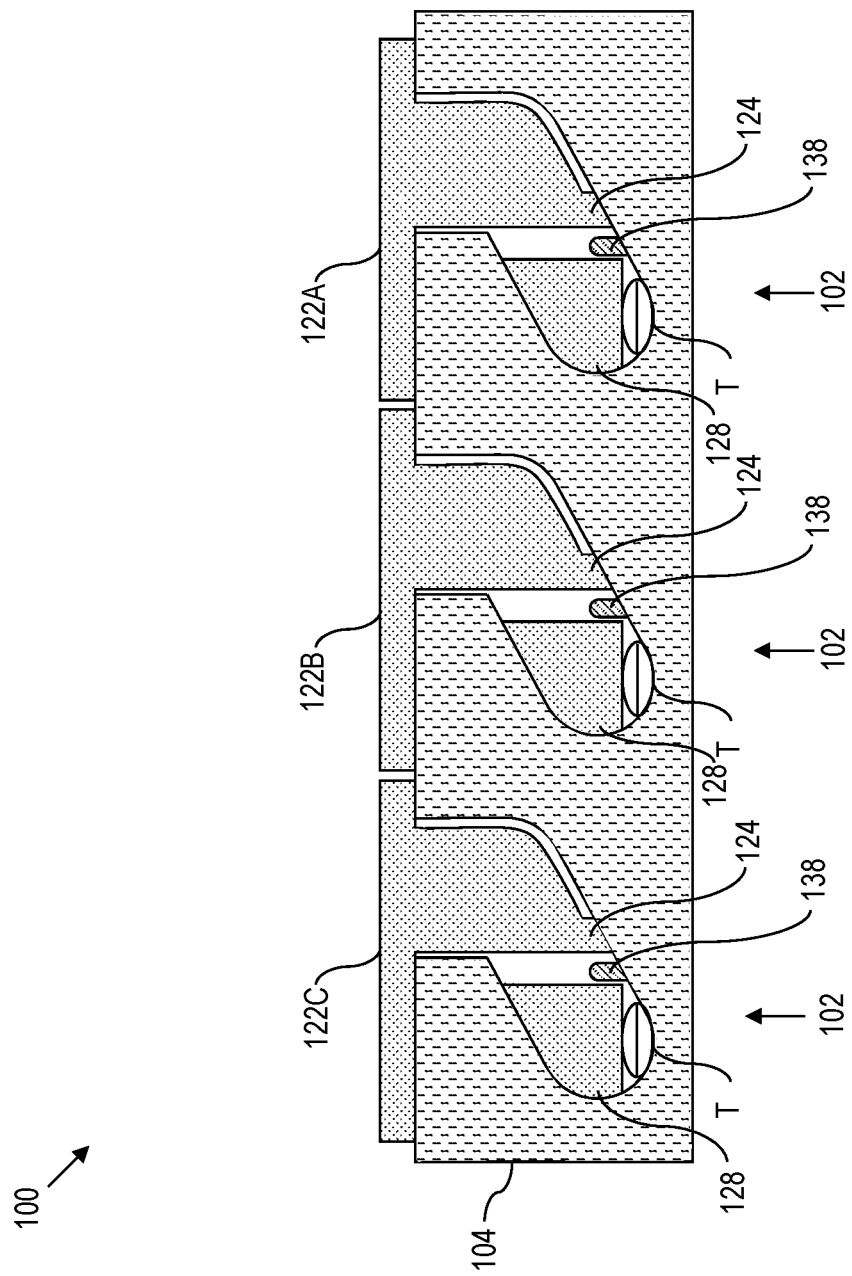
FIG. 14 is a front side view of a simplified tube holder, according to aspects of the present disclosure herein.
Figure 15:
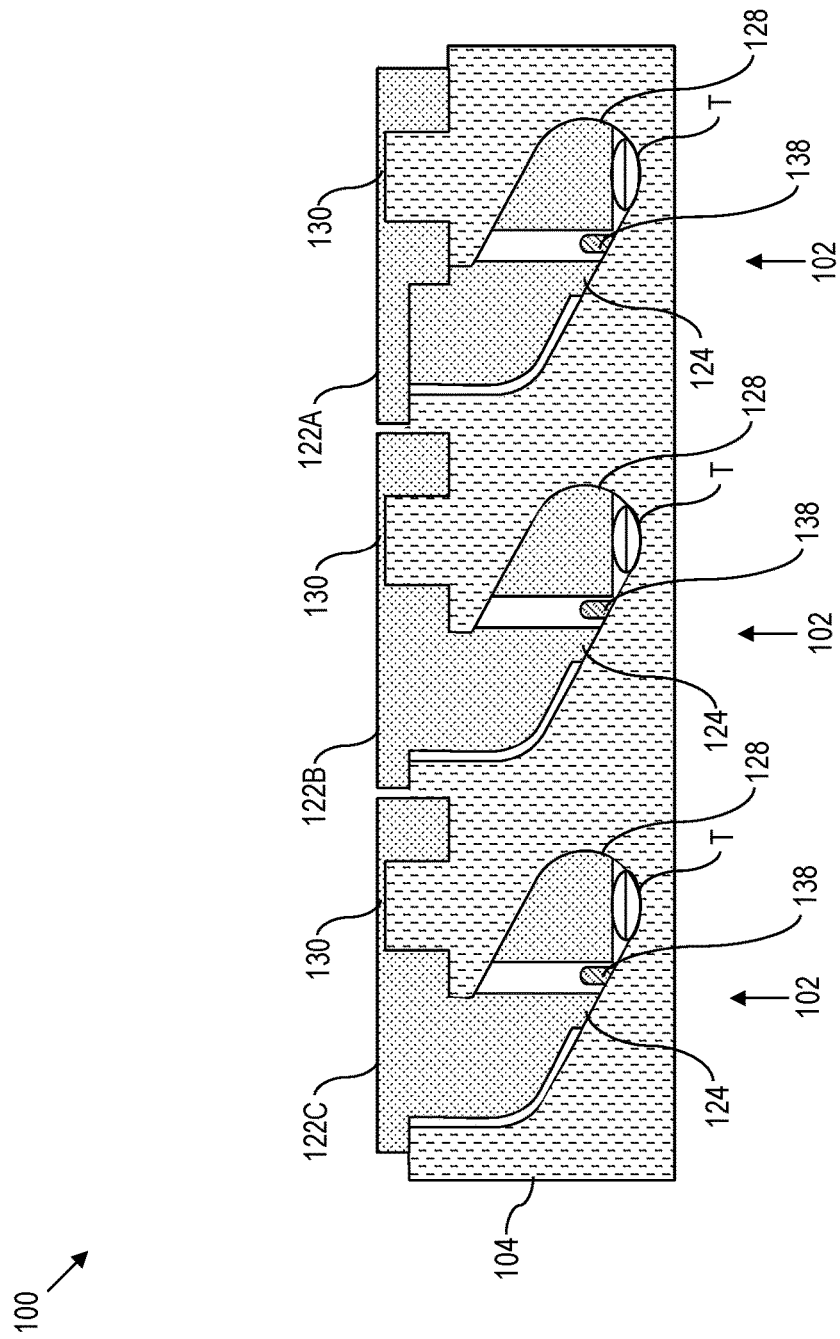
FIG. 15 is a back side view of the simplified tube holder of FIG. 14, according to aspects of the present disclosure herein.

Referring to FIG. 14 and FIG. 15, a front an back view respectively, of a tube holder 100 is illustrated in simplified schematic form. The tube holder 100 is identical to the tube holder described herein with regard to the previous FIGURES, but with certain features omitted or illustrated in simplified schematic form for clarity of discussion. Notably, the handle lever 122A, the handle lever 122B, and the handle lever 122C are each hinged via hinge 130 to the second (closed) position. Since each tube clamp 102 is independent, the illustrated state is purely arbitrary and each tube clamp 102 can be in an open or closed state.

Notably, as illustrated, when the lever handle 122A is in the closed position, the gate 124 closes off the second tube passageway 112 from the tube receiving channel 114. The gate 124 cooperates with the barricade 138, thus preventing a tube "T" peripherally inserted into the tube receiving channel 114 from exiting the tube holder 100.

Also as illustrated, the tube pinch 128 compresses the volume within the tube receiving channel 114 sufficient to deform the flexible tube T, thus pinching the tube and preventing fluid flow through the pinch point.

Figure 16:
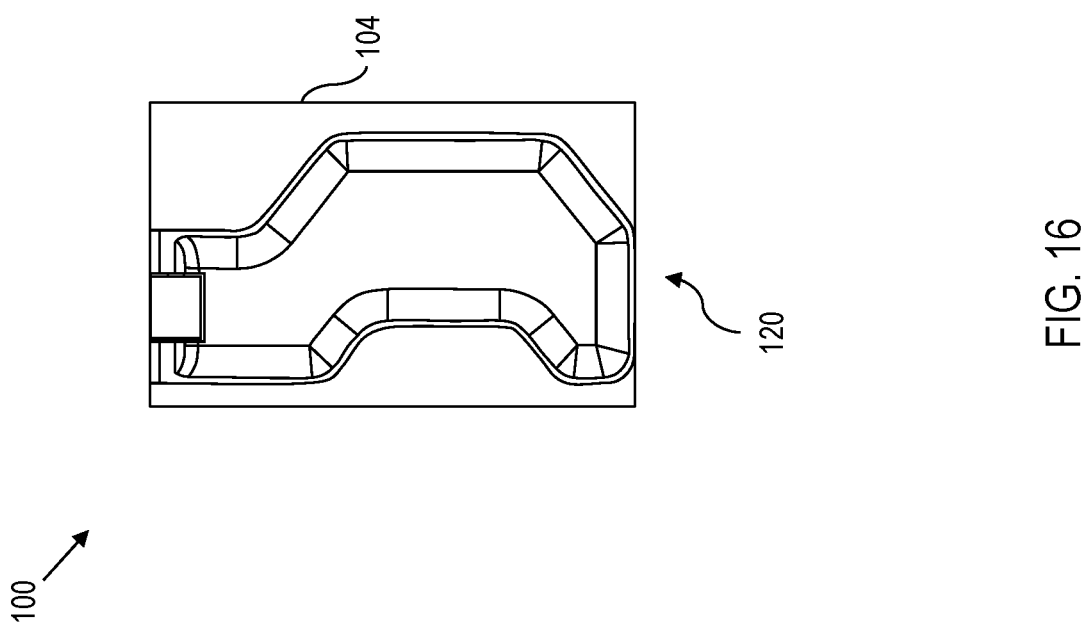
FIG. 16 illustrates a single tube clamp.
Figure 17:
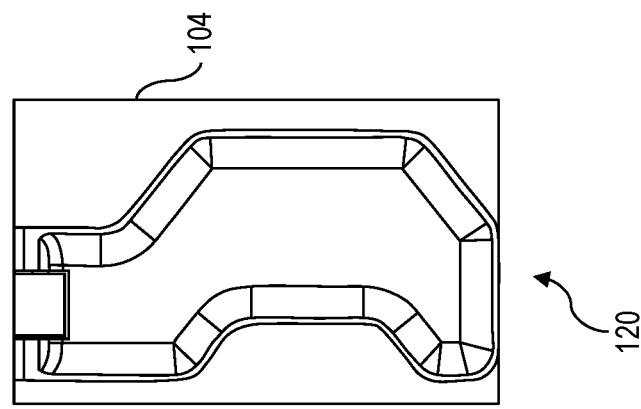
FIG. 17 illustrates an arbitrary number of independent tube clamps positioned adjacent to one another.
Figure 17:
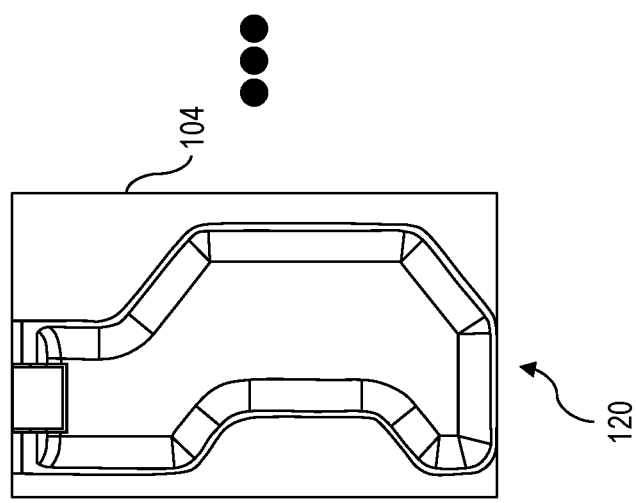
Figure 17:
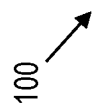

Referring generally to FIG. 16 and FIG. 17, embodiments are illustrated where a tube holder 100 includes a single tube clamp (FIG. 16), or an arbitrary number of tube clamps (FIG. 17). Notably, FIG. 17 illustrates a first tube clamp, and at least one additional tube clamp, the at least one additional tube clamp being identical in function to the first tube clamp and positioned laterally adjacent to the first tube clamp. Here, the tube clamps can be provided in a common housing, or each tube clamp can be in a separate housing that are situated adjacent to each other. In the later example, a carrier, holder, carton or other structure can be used to keep the tube clamps together.

Miscellaneous

Aspects herein provide a tube lock and tube clamp that provide definitive access and tracking to medical use tube lines, e.g., PICC lines. In this regard, the tube lock described herein can be added to any PICC line system, without requiring modification of the PICC line itself. Moreover, because the lock can be electronically controlled, individual access and/or authority can be granted to select individuals, or based upon other measurable attribute, e.g., job code. The tube lock is tamper proof, and because of the lock design, can be configured to fail in a locked mode. As such, the tube lock can, for instance, prevent patients from using their PICC lines as a source for opioid or other drug-related overdose while allowing healthcare systems to safely transition patients receiving ongoing intravenous therapies to an outpatient setting. This safe transition could result in a reduction of billions of dollars in uncompensated healthcare for health systems.

Aspects herein provide a tube lock design that allows each tube to be inserted into an individual clamp set. For instance, an individual clamping release mechanism can be provided for each tube. Moreover, the system can be expanded to include an unlimited number of tubes, e.g., run in parallel. Moreover, aspects herein provide a tube lock that is scalable. For instance, tubing diameter can range from micro-tubing to large diameter tubes. Some embodiments enable peripheral insertion of a tube. This allows for clamping to be added independent of the tubing manufacturing process. As such, the tube clamp and/or tube lock does not have to be integrated into the manufacturing process of existing PICC-line systems.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Aspects of the disclosure were chosen and described in order to best explain the principles of the disclosure and the practical application, and to enable others of ordinary skill in the art to understand the disclosure for various embodiments with various modifications as are suited to the particular use contemplated.

What is claimed is:

1. A tube lock comprising:
a lock housing comprising a tube clamp compartment, the tube clamp compartment having a clamp compartment opening therein;
a clamp cover that mates with the lock housing to provide a barrier over the clamp compartment opening of the tube clamp compartment; and
a tube clamp within the tube clamp compartment, the tube clamp having:
a housing having a tube entry along a major surface thereof;
a first tube passageway that extends from the tube entry into the housing;
a tube receiving channel coupled to the first tube passageway; and
a clamping mechanism, the clamping mechanism having:
a lever handle user operable to transition from a first position to a second position;
a tube pinch coupled to the lever handle;
wherein:
when a tube is peripherally inserted so as to pass from the tube entry through the first tube passageway and into the tube receiving channel and the lever handle of the clamping mechanism is in the second position:
the tube clamp pinches the tube so as to prevent a flow of a fluid through the tube; and
when the clamp cover is mated with the lock housing, the lever handle of the clamping mechanism is prevented from transitioning from the second position to the first position, thus locking the tube inserted into the tube clamp.

2. The tube lock of claim 1, wherein:
the tube clamp compartment of the lock housing has a cover slot separate from the clamp compartment opening;
the clamp cover includes an overbite that receives the cover slot in the tube clamp compartment when the clamp cover is in a closed position.

3. The tube lock of claim 2, wherein:
the clamp compartment opening is formed in a top of the clamp compartment;
the cover slot is formed in a side of the clamp compartment;
the clamp cover includes a lid that extends over the top of the clamp component, and a side cover that extends from the lid over the side of the clamp compartment having the cover slot; and
the overbite is included on the side cover.

4. The tube lock of claim 2, wherein:
the lock housing further comprises a lock compartment having a first cover hinge slide channel and second cover hinge slide channel;
the clamp cover comprises a hinge component having a first end and a second end; and
the first end of the hinge component engages the first cover hinge slide channel and the second end of the hinge component engages the second cover hinge slide channel, such that the clamp cover can slide laterally towards the tube clamp compartment.

5. The tube lock of claim 4, wherein:
when the clamp cover is unlocked, the first cover hinge slide channel and the second cover hinge slide channel enable the clamp cover to slide laterally across the tube clamp compartment of the lock housing, thus pushing the overbite out from the cover slot.

6. The tube lock of claim 1, wherein:
the lock housing further comprises a control compartment and a lock compartment;
further comprising:
a cover lock positioned in the lock compartment that is controlled to transition between a locked state and an unlocked state, the cover lock further configured to lock the clamp cover to the lock housing when the lock is in the locked state; and
electronics within the control compartment that electronically control the cover lock to transition between the locked state and the unlocked state.

7. The tube lock of claim 6, wherein:
the electronics comprise:
a controller communicably coupled to the cover lock; and
a wireless device communicably coupled to the controller, and
the controller is configured to transition the cover lock from the locked state to the unlocked state responsive to an unlock command received from the wireless device, where the unlock command is wirelessly received by the wireless device.

8. The tube lock of claim 7, wherein:
the wireless device comprises a near field communications device that responds to a corresponding remote tag.

9. The tube lock of claim 7, wherein:
the wireless device comprises a radio frequency identification device that responds to a corresponding remote tag.

10. The tube lock of claim 7, wherein:
the electronics further comprise memory communicably coupled to the controller; the controller operatively configured to store in the memory, an identifier of an operator that unlocks the cover lock by reading an identifier code in a communication received by the wireless device.

11. The tube lock of claim 7, wherein:
the cover lock is coupled to a linear actuator that is controlled by the controller to transition the cover lock between the locked state and the unlocked state.

12. The tube lock of claim 11, wherein:
the cover lock comprises a shaft having a shaft lock positioned therealong;
the clamp cover includes at least one wedge;
the linear actuator linearly moves the shaft so as to shift the shaft lock into an interference position with the wedge when in the locked state; and
the linear actuator linearly moves the shaft so as to shift the shaft lock into an avoidance position with the wedge when in the unlocked state.

13. The tube holder of claim 1, wherein:
a gate extends from the lever handle; and
the clamping mechanism is configured such that:
when the lever handle is in the first position, the gate exposes the tube receiving channel to the first tube passageway and the tube clamp is disposed in an unclamped position relative to the tube receiving channel;

when the lever handle is in the second position, the gate at least partially blocks the tube receiving channel from the first tube passageway, and the tube clamp is disposed in a clamped position relative to the tube receiving channel; and the clamping mechanism is further configured such that when the lever handle is in the second position, the lever handle at least partially covers the tube entry.

14. The tube holder of claim 1, wherein:

the tube entry extends across the entire major surface of the housing;

the first tube passageway defines a first passthrough that slots through the housing from a front face through to a back face, where the front face and back face define surfaces that are adjacent to the major surface;

the first tube passageway extends from the tube entry into the housing in a direction perpendicular to the major surface;

a second tube passageway connects the first tube passageway to the tube receiving channel, wherein the second tube passageway extends angularly into the housing from the first tube passageway; and the second tube passageway defines a second passthrough that slots through the housing from the front face through to the back face.

15. A tube lock comprising:

a lock housing comprising:
- a tube clamp compartment, the tube clamp compartment having an clamp compartment opening therein; and
- a lock compartment;

a clamp cover that mates with the lock housing to provide a barrier over the clamp compartment opening;

a cover lock positioned in the lock compartment that is controlled to transition between a locked state and an unlocked state, the cover lock further configured to lock the clamp cover to the lock housing when the cover lock is in the locked state; and electronics within the lock housing that electronically control the cover lock to transition between the locked state and the unlocked state;

wherein:
when a tube clamp having a lever handle is inserted into the clamp compartment and the clamp cover is mated with the lock housing, the lever handle is prevented from lifting sufficient to peripherally release a tube held by the tube clamp.

16. The tube lock of claim 15, wherein:

the tube clamp compartment of the lock housing has a cover slot separate from the clamp compartment opening;

the clamp compartment opening is formed in a top of the clamp compartment;

the cover slot is formed in a side of the clamp compartment;

the clamp cover includes a lid that extends over the top of the clamp component, and a side cover that extends from the lid over the side of the clamp compartment having the cover slot; and the side cover includes an overbite that receives the cover slot in the tube clamp compartment when the clamp cover is in a closed position.

17. The tube lock of claim 15, wherein:

the electronics comprise:
- a controller communicably coupled to the cover lock; and
- a wireless device communicably coupled to the controller, the cover lock is coupled to a linear actuator that is controlled by the controller to transition the cover lock between the locked and unlocked states; and the controller is configured to transition the cover lock from the locked state to the unlocked state responsive to an unlock command received from the wireless device, where the unlock command is wirelessly received by the wireless device.

18. The tube lock of claim 15 further comprising:

a tube clamp within the tube clamp compartment, the tube clamp having:
- a tube receiving channel extending across a tube clamp housing configured to receive a tube;
- a clamping mechanism having a lever handle user operable to transition from a first position to a second position;

wherein:
when a tube is positioned in the tube receiving channel and the lever handle of the clamping mechanism is in the second position, the tube clamp pinches the tube so as to prevent a flow of a fluid through the tube.

19. A tube lock comprising:

a lock housing comprising a tube clamp compartment and a lock compartment;
the tube clamp compartment having an clamp compartment opening therein;

a clamp cover that mates with the lock housing to provide a barrier over the clamp compartment opening;

a linear actuator within the lock housing;

a cover lock positioned in the lock compartment that is controlled by the linear actuator to transition between a locked state and an unlocked state, the cover lock further configured to lock the clamp cover to the lock housing when the cover lock is in the locked state;

electronics within the lock housing that electronically control the cover lock to transition between the locked state and the unlocked state, the electronics including:
- a controller communicably coupled to the lock; and
- a wireless device communicably coupled to the controller, and a tube clamp within the tube clamp compartment, the tube clamp having:
- a tube receiving channel extending across a tube clamp housing configured to receive a tube;
- a clamping mechanism having a lever handle user operable to transition from a first position to a second position;

wherein:
when a tube is positioned in the tube receiving channel and the lever handle of the clamping mechanism is in the second position, the tube clamp pinches the tube so as to prevent a flow of a fluid through the tube;

when the clamp cover is mated with the lock housing, the lever handle of the clamping mechanism is prevented from transitioning from the second position to the first position, thus locking the tube inserted into the tube clamp; and the controller is configured to transition the cover lock from the locked state to the unlocked state, thus unlocking the clamp cover, responsive to an unlock command received from the wireless device, where the unlock command is wirelessly received by the wireless device.

* * * * *